United States Patent
Hakim

(10) Patent No.: US 9,867,774 B1
(45) Date of Patent: *Jan. 16, 2018

(54) BODY LOTION

(71) Applicant: Noha N. Hakim, Easton, PA (US)

(72) Inventor: Noha N. Hakim, Easton, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/238,420

(22) Filed: Aug. 16, 2016

(51) Int. Cl.
| | |
|---|---|
| *A61K 8/97* | (2017.01) |
| *A61K 8/19* | (2006.01) |
| *A61K 8/34* | (2006.01) |
| *A61K 8/73* | (2006.01) |
| *A61K 8/92* | (2006.01) |
| *A61Q 19/00* | (2006.01) |

(52) U.S. Cl.
CPC ............. *A61K 8/97* (2013.01); *A61K 8/19* (2013.01); *A61K 8/34* (2013.01); *A61K 8/73* (2013.01); *A61K 8/732* (2013.01); *A61K 8/92* (2013.01); *A61K 8/922* (2013.01); *A61Q 19/007* (2013.01); *A61K 2800/87* (2013.01)

(58) Field of Classification Search
CPC ... A61K 8/97; A61K 8/19; A61K 8/34; A61K 8/73; A61K 8/732; A61K 8/92; A61K 8/922; A61K 2800/87; A61Q 19/007
See application file for complete search history.

(56) References Cited

U.S. PATENT DOCUMENTS

| | | | | |
|---|---|---|---|---|
| 5,741,766 | A * | 4/1998 | Marion | A61K 8/06 424/401 |
| 2012/0201902 | A1* | 8/2012 | Modak | A01N 31/02 424/618 |
| 2013/0045278 | A1* | 2/2013 | Qian | A61K 36/82 424/528 |
| 2015/0238409 | A1* | 8/2015 | Eizen | A61K 8/922 424/602 |
| 2015/0290120 | A1* | 10/2015 | Nalabolu | A61K 8/97 424/727 |

FOREIGN PATENT DOCUMENTS

CN        1261532 A  *  8/2000

OTHER PUBLICATIONS

English Translation of CN 1261532 A. Retrieved and Translated from Google Patent Mar. 2, 2017.*

* cited by examiner

*Primary Examiner* — Anoop K Singh
*Assistant Examiner* — Doan T Phan
(74) *Attorney, Agent, or Firm* — Gary P. Topolosky

(57) ABSTRACT

This invention is a natural lotion that exploits the benefits of Dead Sea salt for helping with the dry skin of a human body, especially on the arms, legs, hands and face. The lotion adds to a base of organic aloe vera juice, organic coconut oil, shea butter, sunflower oil, olive oil, NF emulsified wax (vegetable based), rose hydrosol, and apple cider vinegar. It also includes green tea extract and several pure essential oils like geranium, bergamot, sweet orange and patchouli.

13 Claims, No Drawings

BODY LOTION

BACKGROUND

The skin for the human body secretes slightly acidic natural oil called sebum to protect it from becoming too dry. Dry skin is a condition, not a disease, and can be caused by using harsh soaps, itchy clothing, unsuitable body moisturizers, hot and cold weather, hard water and diet. Also medications for such medical conditions as diabetes, psoriasis, hypothyroidism, and malnutrition may cause severe dry skin. See generally, http://www.webmd.boots.com/healthy-skin/guide/causes-dry-skin.

Some signs of dry skin on the human body include itching, flaking, skin redness and cracks, skin tightness after shower. See, http://www.mayoclinic.org/diseases-conditions/dry-skin/basics/symptoms/con-20030009.

The lotion of this invention is especially noted for use with the skin of a human body, particularly the skin on one's arms, legs, hands and face.

FIELD OF THE INVENTION

This invention relates to body lotions. Particularly, it relates to lotions for helping the skin avoid dehydration, dryness and to reduce other skin symptoms including itching, flaking or cracking. Preferred composition will be sold under the SeaLand Cosmetics™ brand.

The SeaLand Cosmetics Body Lotion is a unique combination of salt from the Dead Sea and the earth's natural ingredients such as organic Aloe Vera, organic coconut oil, olive oil, shea butter, sunflower oil, apple cider vinegar, rose hydrosol and green tea extract along with several, specially selected pure essential oils. This particular formulation will help hydrate and moisturize the skin of the human body when applied externally on arms, hands, legs and face. Also, it will keep the skin at its normal acid mantle pH (4.0-6.0).

To assure safety of the product, SeaLand Cosmetics uses in the body lotion a combination of the natural preservative Leucidal® liquid (a plant based *leuconostoc*/radish root ferment filtrate) and phenoxyethanol which is a nature identical chemical that can be found in green tea and produced by treating phenol with ethylene oxide in an alkaline medium that reacts to form a pH balanced ingredient. This synthetically produced commercial ingredient does not release formaldehyde or cause health risks thus assuring safety of the product. One commercial product is Optiphen® Plus and is used with <1.0% in the body lotion formulation of this invention. Should Optiphen no longer be commercially available, substantially equivalent alternatives may be substituted therefor.

RELATED ART

Dead Sea salt, as removed from waters from the Dead Sea water, is a known component for various preferred end uses.

Biener U.S. Pat. No. 4,943,432 added such salts to magnesium halide, several alkaline earth metal salts and other cations as part of a composition for treating psoriasis.

Stravroff et al. U.S. Pat. No. 5,866,145 mixed Dead Sea salts with some silicone oils and fragrances to serve as a moisturizing body "polisher".

Maor et al. U.S. Pat. No. 6,582,709 discloses a pharmaceutical cream composition for the treatment of skin disorders, said composition including about 1-6 wt. % Dead Sea mud as an active ingredient.

Lucenta U.S. Published Application No. 20110229419 mixed Dead Sea salt with sodium chloride for the prevention and healing of canker sores.

And Samuelson et al. U.S. Pat. No. 9,050,273 discloses using ultra fine Dead Sea mineral compounds in compositions for use in bath and body products.

The Dead Sea is one of the most saline lakes in the world. It lies between e hills of Judaea to the west and the Trans-Jordanian plateaus to the east. The Jordan River flows from the north into the Dead Sea. About 2.5 million years ago; heavy stream flow into the lake deposited thick sediments containing shale, clay, sandstone, rock salt, and gypsum. After this, strata of clay, marl, soft chalk, and gypsum fell upon layers of sand and gravel.

Having no outlet, the Dead Sea is a "terminal lake" meaning that it loses huge amounts of water by evaporation in the hot dry air. The water has evaporated faster than it has been replenished by precipitation over the last 10,000 years. That results in the lake gradually shrinking to its present form. Because of this, bare deposits cover the Dead Sea valley to a thickness of 1 to 4 miles (1.6 to 6.4 km). This water evaporation has also resulted in high concentrations of salts and minerals in a unique composition particularly rich in magnesium, sodium, potassium, calcium, bromide and various other minor anions such as, e.g., sulfate.

The concentration of salt increases as one descends toward the bottom of the Dead Sea. Down to 130 feet (40 m), the temperature varies from 66 to 98° F. (19 to 37° C.), and the salinity is slightly less than 300 parts per thousand. At this depth, the water is particularly rich in sulfates and bicarbonates. There is a transition zone located between 130 and 330 ft. (40 and 100 m). The lower waters below 330 ft. (100 m) have a uniform temperature of about 72° F. (22° C.) and a higher degree of salinity (approximately 332 parts per thousand). This lower water contains hydrogen sulfide along with strong concentrations of magnesium, potassium, chlorine, and bromine. Below that level, the deepest waters are saturated with sodium chloride that precipitates to the bottom.

The lower waters of the Dead Sea are fossilized; they remain permanently on the bottom because they are very salty and dense. The upper waters date from a few centuries A.D.

The Dead Sea's mineral composition differs from that of ocean water; the salt in most oceans is approximately 85% sodium chloride while Dead Sea salt is only 12-18% sodium chloride. An analysis of major ion concentrations in the water of the Dead Sea gave the following results. (Reference 1, below)

The major ions in Dead Sea water are:

| Ion | Concentration (mg/L) |
| --- | --- |
| Chloride and Bromide | 230,400 |
| Magnesium | 45,900 |
| Sodium | 36,600 |
| Calcium | 17,600 |
| Potassium | 7,800 |

The Dead Sea's overall salt concentration is 340 g/L according to Reference 1. One study concluded that the high concentration of Mg in Dead Sea salt made it instrumental in improving skin hydration and reducing inflammation (Reference 2). According to Reference 3, the high concentration of bromide and magnesium in Dead Sea salt can cleanse and detoxify the skin and body. References 4 and 5 both address bathing in a Mg-rich, Dead Sea salt solution.

REFERENCES

1. Kuehl B L, Fyfe K S, Shear N H (March 2003). "*Cutaneous cleansers*". Skin Therapy Lett 8 (3): 1-4. PMID 12858234.
2. Pierce J D Jr, Zeng X N, Aronov E V, Preti G, Wysocki C J (August 1995). "*Cross-adaptation of sweaty-smelling 3-methyl-2-hexenoic acid by a structurally similar, pleasant-smelling odorant*". Chem Senses 20 (4): 401-11. doi: 10.1093/chemse/20.4.401. PMID 8590025.
3. Ma'or, Zeev et al. "*Antimicrobial properties of Dead Sea black mineral mud*", International Journal of Dermatology, May 2006. Retrieved on 2008 Apr. 13.
4. Proksch, Ehrhardt M D, PhD et al. "*Bathing in a magnesium-rich Dead Sea salt solution improves skin barrier function, enhances skin hydration, and reduces inflammation in atopic dry skin*", International Journal of Dermatology, February 2005. Retrieved 2008 Apr. 13.
5. Ehrhardt, Proksch; Nissen, H P; Bremgartner, M; Urquhart, C. "*Bathing in a magnesium-rich Dead Sea salt solution: follow-on review*". International Journal of Dermatology 46 (2): 177-179. doi: 10.1111/j.1365-4632.2005.02079.x. PMID 15689218.

SUMMARY OF THE INVENTION

A first object of the invention is to create a natural formulation that contains 4% Dead Sea salt for humans use to improve skin hydration and reducing inflammation. It will be used to help to treat symptoms of dry skin especially on the legs, arms, hands and face areas of the body.

A second object is to create a pH-balanced skin formulation. That formulation is slightly acidic with a pH between 4.0 and 6.0. It will be used to help maintain the thin, protective layer on skin surface hat is called the acid mantle. This natural formulation of body lotion for the human body; especially the arms; hands, legs and face, includes natural ingredients such as organic aloe vera juice, organic coconut oil, olive oil, sunflower oil, shea butter, apple cider vinegar, rose hydrosol and a green tea extract along with pure essential oils such as geranium, bergamot, sweet orange and patchouli. They will all work in harmony to help moisturize the skin and reduce symptoms of dry skin especially in the legs, arms, hands and face areas.

These protective oils, waterproof skin and help keep the skin cells tight and flat (like roof shingles), protecting you from the elements like wind, cold and water. They also make it harder for bacteria and other microbes to get a toe-hold on one's skin.

A third object is to assure the safety of the product by adding a natural plant based preservative (Leucidal® liquid) and phenoxyethanol (Optiphen® Plus), the listed ingredients of which include phenoxyethanol, caprylyl glycol and sorbic acid. Natural preservatives are also included in the organic aloe vera juice, particularly potassium sorbate and citric acid. Note that this body lotion product does not contain any ingredients like triclosan, phthalates, soy or gluten.

DESCRIPTION OF PREFERRED EMBODIMENTS

Ideally, the composition of this Body moisturizing lotion includes the following in addition to its main novel ingredient of Dead Sea salt.

Aloe Vera Juice:

It is used instead of water as a diluent; the juice is made of the whole Aloe Vera leaves to include inner gel which soothes the skin and serve as an anti-inflammatory. The herb can be an effective moisturizing agent and has antimicrobial properties against many common bacteria and fungi.

Organic Coconut Oil:

Coconut oil contains saturated medium chain fatty acids or triglycerides which retain the moisture content of the skin and eliminate moisture loss through the pores on skin. Also the presence of capric/caprylic/lauric acid in coconut oil has strong disinfectant and antimicrobial properties.

Olive Oil:

Olive oil is composed mainly of the mixed triglyceride esters of oleic and palmitic acids and other fatty acids plus other nutrients like vitamins A and E to act as natural humectant that actually helps to attract moisture to dry skin.

When olive oil blends well with coconut oil before adding it to the formula, it decreases the chance of the organic coconut oil to convert back to its solid state in cold environment and increases the stability of the formulation.

Sunflower Oil:

The oil is light in texture, non-greasy and can be absorbed quickly. The main component of sunflower oil is linoleic acid and other components include oleic acid, palmitic acid and vitamins such as A, D and E; these components make the oil a good hydrating agent.

Shea Butter:

The concentration of natural vitamins (A, E and F) and fatty acids such as oleic, stearic, palmitic and linolenic acids in Shea butter help to moisturize skin and provides the nutrients necessary for collagen production. Also, the presence of Cinnamic compounds help to reduce inflammation and may offer UV protection (it is SPF ~6). See, generally, http://www.ncbi.nlm.nih.gov/pubmed/20484832.

NF Emulsifying Wax (Vegetable Based):

It is used to form emulsion between water and oil ingredients by attracting them to different portions of its structure (hydrophilic for water molecules and hydrophobic for oil molecules).

Apple Cider Vinegar:

It keeps the pH of this body lotion on the acidic side plus it has antiseptic, anti-fungal and anti-bacterial properties that relieves itching symptom of dry skin.

Rose Hydrosol:

Rose water hydrates, revitalizes and moisturizes the skin, and makes it smooth.

Preservatives:

One preferred set of preservatives for use in this product consists of:

(i) 1.4% natural preservative called Leucidal® liquid, it is a product derived from radishes fermented with *leuconostoc kimchii*, a lactic acid bacteria that has traditionally been used to make kimchi, this product consists of an isolated peptide that is secreted from the bacteria during the fermentation process that has been shown to have antimicrobial benefits. Leucidal® liquid is accepted by ECOcert as an ingredient in certified organic cosmetics. and (ii) 0.6% phenoxyethanol. Though the latter is not natural, it is the only synthetic preservative which: doesn't release formaldehyde, works well with formulas having a pH less than 6 and which causes the least skin irritation. One representative off-the-shelf preservative is a product called Optiphen® Plus, the listed ingredients of which include phenoxyethanol, caprylyl glycol and sorbic acid.

Green Tea Extract:

The medicinal properties of tea are attributed to flavonoid phytochemicals called polyphenols. The polyphenols found in tea mainly belong to the subtype called catechins. Green tea appears to exert sun damage protection by quenching free radicals and reducing inflammation rather than by blocking UV ray.

Pure Essential Oils:

Geranium: The main components of geranium oil are citronellol (26.7 percent) and geraniol (13.4 percent). They can help eliminate the appearance of scars and dark spots by improving blood circulation just below the surface of the skin and promoting an equal distribution of melanin.

Bergamot: Bergamot has citrusy smell and is known for its ability to distribute pigments evenly throughout the skin, leaving an even, toned complexion. Also it helps to control foul body odors by keeping the bacterial populations low.

Sweet Orange: The most prominent active ingredients in orange oil are limonene (which is about 85-96% of the extract). Limonene is especially considered a powerful antioxidant that fights free radical damage and inflammation.

Patchouli: Patchouli oil has strong sweet, spicy and musky aroma that has the ability to eliminate or mask body odor. Also it has the ability to help alleviate such issues as acne-prone conditions, eczema, inflammation, and cracked, chapped, irritated skin.

The potato starch and xanthan gum are purposefully additives for lotion thickening.

EXAMPLE

A typical sales quantity of this body lotion would be packaged in 4 oz. container. A main formula for that lotion according to this invention consists of:

Organic aloe vera juice 66%
Organic coconut oil 6%
Dead Sea salt 4%
Potato starch 1.8%
Olive oil 3%
NF emulsified wax (vegetable based) 4%
Rose hydrosal 2%
Leucidal® liquid 1.4%
Apple cider vinegar 1%
Phenoxyethanol (Optiphen Plus) 0.6%
Shea butter 5%
Sunflower oil 3%
Green tea extract and pure essential oils 2% (Geranium, Bergamot, Sweet Orange, Patchouli)
Xanthan gum 0.2%

It should be noted that the organic aloe vera juice used in this formula contains natural preservatives, particularly potassium sorbate and citric acid.

Preferred embodiments of this body lotion offer a pH-balanced formula (accomplished by adding together apple cider vinegar and the pure essential oils). The aforesaid combination of components achieves a pH in the range of about 4-6.

The aforementioned ingredients are mixed altogether and bottled in a 4 oz. plastic container with pump dispenser lid. Directions for use of this invention are as follows:

First shake the container/bottle before applying to the user's clean skin. Massage it onto the skin and applied it as much as needed.

If the user suspects an allergic reaction, he/she should discontinue further uses and consult a physician.

While the invention has been described with a certain degree of particularity, it is manifest that many changes may be made in the arrangement of components without departing from the spirit and scope of this disclosure. It is understood that the invention is not limited to the embodiments set forth herein for purposes of exemplification, but s to be limited only by the scope of the attached claim or claims.

What is claimed is:

1. A lotion for hydrating and moisturizing skin on a human body area selected from the group consisting of an arm, a leg, a hand and a face, said lotion comprising:
    (a) about 62-72 wt. % organic aloe vera juice,
    (b) about 4-8 wt. % organic coconut oil,
    (c) about 3-5 wt. % Dead Sea salt,
    (d) about 1-3 wt. % potato starch,
    (e) about 4-6 wt. % shea butter,
    (f) about 2-4 wt. % olive oil,
    (g) about 2-4 wt. % sunflower oil,
    (h) about 3-5 wt. % emulsified wax,
    (i) about 1-3 wt. % rose hydrosol,
    (j) about 0.5-1.5 wt. % apple cider vinegar,
    (k) about 1-3 wt. % pure essential oils and green tea extract, and
    (l) about 0.1-0.3% xanthan gum.

2. The lotion of claim 1 wherein the pure essential oils include geranium, bergamot, sweet orange and patchouli.

3. The lotion of claim 1 wherein said lotion comprises:
    (a) about 66 wt. % organic aloe vera juice,
    (b) about 6 wt. % organic coconut oil,
    (c) about 4 wt. % Dead Sea salt,
    (d) about 1.8 wt. % potato starch,
    (e) about 5 wt. % shea butter,
    (f) about 3 wt. % olive oil,
    (g) about 3 wt. % sunflower oil,
    (h) about 4 wt. % emulsified wax,
    (h) about 2 wt. % rose hydrosol,
    (i) about 1 wt. % apple cider vinegar,
    (j) about 2 wt. % pure essential oils and green tea extract, and
    (k) about 0.2 wt. % xanthan gum.

4. The lotion of claim 1 wherein the pH of the lotion is between about 4.0 and 6.

5. A lotion for hydrating and moisturizing a human body arm, leg, hand or face, said lotion comprising:
    (a) about 62-72 wt. % organic aloe vera juice,
    (b) about 4-8 wt. % organic coconut oil,
    (c) about 3-5 wt. % Dead Sea salt,
    (d) about 1-3 wt. % potato starch,
    (e) about 4-6 wt. % shea butter,
    (f) about 2-4 wt. % olive oil,
    (g) about 2-4 wt. % sunflower oil,
    (h) about 3-5 wt. % emulsified wax,
    (i) about 1-3 wt. % rose hydrosol,
    (j) about 0.5-1.5 wt. % apple cider vinegar, and
    (k) about 1-3 wt. % pure essential oils and green tea extract
    (l) about 1.4-2.8 wt. % of a preservative and
    (m) about 0.1-0.3% xanthan gum.

6. The lotion of claim 5 wherein the preservative consists essentially of:
    (i) about 1-1.8 wt. % of a *leuconostoc*/radish root ferment filtrate; and
    (ii) about 0.4-1.0 wt. % phenoxyethanol.

7. The lotion of claim 5 wherein the pure essential oils include geranium, bergamot, sweet orange and patchouli.

8. A method for hydrating and moisturizing dry skin symptoms on a human body area, said method comprising:
    (i) providing a lotion composition comprising:
        (a) about 62-72 wt. % organic aloe vera juice,
        (b) about 4-8 wt. % organic coconut oil,
        (c) about 3-5 wt. % Dead Sea salt, (d) about 1-3 wt. % potato starch,
(e) about 4-6 wt. % shea butter,
(f) about 2-4 wt. % olive oil,
(g) about 2-4 wt. % sunflower oil,
(h) about 3-5 wt. % emulsified wax,
(i) about 1-3 wt. % rose hydrosol,
(j) about 0.5-1.5 wt. % apple cider vinegar,
(k) about 1-3 wt. % pure essential oils and green tea extract,
(l) about 1.4-2.8 wt. % of a preservative, and
(m) about 0.1-0.3 wt % Xanthan gum;
(ii) supplying the lotion composition in a dispenser for applying to the skin of the human; and
(iii) applying the lotion composition from the dispenser to the human body area in need thereof.

9. The method of claim 8 wherein the preservative in the lotion composition consists essentially of:
(i) about 1-1.8 wt. % of a *leuconostoc*/radish root ferment filtrate; and
(ii) about 0.4-1 wt. % phenoxyethanol.

10. The method of claim 8 wherein the blend of pure essential oils tracts includes: geranium, bergamot, sweet orange and patchouli.

11. The method of claim 8, wherein the body area is a human arm or leg.

12. The method of claim 8, wherein the body area is a human hand.

13. The method of claim 8, wherein the body area is a human face.

\* \* \* \* \*